United States Patent [19]
Dandekar et al.

[11] Patent Number: 5,523,326
[45] Date of Patent: Jun. 4, 1996

[54] PSA PROCESS WITH REACTION FOR REVERSIBLE REACTIONS

[75] Inventors: Hemant W. Dandekar, Chicago; Gregory A. Funk, Carol Stream, both of Ill.; John D. Swift, Hindhead, England; Richard T. Maurer, Nanuet, N.Y.

[73] Assignee: UOP, Des Plaines, Ill.

[21] Appl. No.: 330,780

[22] Filed: Oct. 28, 1994

[51] Int. Cl.$^6$ .................................................. C07C 27/00
[52] U.S. Cl. ...................... 548/706; 518/702; 518/713; 518/724; 518/725
[58] Field of Search ..................................... 518/706, 702, 518/713, 724, 725

[56] References Cited

U.S. PATENT DOCUMENTS

| | | | |
|---|---|---|---|
| 3,176,444 | 4/1965 | Kazuo Kiyonaga | 55/26 |
| 3,430,418 | 3/1969 | Wagner | 55/26 |
| 3,703,068 | 11/1972 | Wagner | 55/21 |
| 3,986,849 | 10/1976 | Fuderer et al. | 55/25 |
| 4,731,387 | 3/1988 | Westerterp | 518/706 |
| 4,968,722 | 11/1990 | Westerterp | 518/706 |
| 5,254,368 | 10/1993 | Kadlec et al. | 423/247 |
| 5,348,707 | 9/1994 | Harandi et al. | 422/129 |

FOREIGN PATENT DOCUMENTS 223332  1/1991  United Kingdom.

OTHER PUBLICATIONS

Alpay E., et al. "Combined Reaction and Separation in Pressure Swing Processes" presented at the International Symposium on Chemical Reaction Engineering, Baltimore, Maryland, Sep. 25-28, 1994.

Cheng, Wu–Hsung and Kung, Harold H., editors, "Methanol Production and Use", New York, Marcel Dekker, Inc., 1994, pp. 51–73.
Kirby, N. F. and Morgan, J.E.P., "A Theoretical Investigation of Pressure Swing Reaction," *Transactions of Industrial Chemical Engineering*, vol. 72, Part A, Jul. 1994, pp.541–550.

*Primary Examiner*—Werren Lone
*Attorney, Agent, or Firm*—Thomas K. McBride; John G. Tolomei; Richard P. Silverman

[57] ABSTRACT

A process is disclosed for the production of methanol from a synthesis gas stream comprising hydrogen and carbon dioxide in which an equilibrium reaction to methanol is achieved by conducting the reaction and the product separation in a pressure swing adsorption and reaction zone containing a uniformly distributed adsorbent for the selective adsorption of methanol and a catalyst for the equilibrium conversion of the synthesis gas to methanol. More specifically, the process achieves the production of methanol by the reaction of the hydrogen and the carbon oxide with the simultaneous adsorption of the product at the same temperature and pressure. The passing of the synthesis stream to the bed is terminated and the bed is purged and depressurized to desorb the methanol product. In one embodiment, the bed is cocurrently purged with at least a portion of an effluent stream prior to depressurizing the bed. In further embodiments, the pressure swing adsorption and reaction zone is employed in a methanol synthesis loop both with and without a secondary reforming step to provide a lean synthesis gas with a stoichiometric ratio of carbon to hydrogen. The use of the pressure swing adsorption and reaction zone results in a higher conversion of the synthesis gas to methanol and significantly reduces the capital and operation costs in the production of methanol by reducing compressor requirements.

38 Claims, 2 Drawing Sheets

ADSORPTION ISOTHERMS AT 200 DEG C

PSA PROCESS WITH REACTION FOR REVERSIBLE REACTIONS

FIELD OF THE INVENTION

This invention pertains to the field of chemical reaction combined with adsorptive separation. More particularly, the invention relates to the combination of pressure swing adsorption processes with reversible chemical reactions. Most particularly this invention relates to the field of producing methanol by a combination of a pressure swing adsorption process and reaction for the production of methanol from a synthesis gas comprising a carbon oxide and hydrogen.

BACKGROUND OF THE INVENTION

Theoretical models of adsorptive reactors which combine multibed pressure swing adsorption and chemical reaction have been studied for some limited types of reversible and irreversible reactions. A paper entitled, "Combined Reaction and Separation in Pressure Swing Processes," by E. Alpay et at. and presented at the International Symposium on Chemical Reaction Engineering, Sep. 25–28, 1994, Baltimore, Md., describes the advantages of such a system for a dissociation reaction producing two components where one of the products is the only adsorbing component. Another paper entitled, "A Theoretical Investigation of Pressure Swing Reaction," by N. F. Kirkby and J. E. P. Morgan, and published in the *TRANSACTIONS OF INDUSTRIAL CHEMICAL ENGINEERING*, Vol. 72, Part A, July 1994, explores a simplified model of pressure swing reaction applied to a non-adsorbable reactant undergoing an irreversible reaction to produce an adsorbable product. These studies indicate that combinations of pressure swing adsorption and reaction have some advantages over conventional reaction systems. The conclusions reached by these studies suggest that the results of the combined PSA and reaction process are significantly different from conventional PSA technology and the steps of the cyclic operation are dependent upon the many variables that relate to the relative adsorption of the products and reactants and the degree to which equilibrium reactions are affected by the adsorption of the reactants and the products of the reaction. To date there have been few commercial applications of combined pressure swing adsorption and reaction where the reactants and the products can be non-adsorbable, less-readily adsorbable and more-readily adsorbable.

Methanol is an important industrial chemical. Because of its simple molecular structure, it is used as a building block for larger, more complicated organic molecules. Traditionally, the primary uses of methanol were for chemical production as a feedstock or as a solvent. Two uses for methanol which will increase the demand for methanol are 1) the requirement for the addition of oxygenates to transportation fuels and 2) the potential use as an agricultural plant growth stimulant. Methanol is used in the manufacture of ethers such as MTBE, methyl tertiary butyl ether, a high octane gasoline blending component, whose increased demand coincides with the worldwide phasedown of lead in transportation fuels.

At present, methanol production is almost exclusively based on a direct hydrogenation of carbon monoxide according to the following equation:

(1)

and if the reactants contain carbon dioxide, also:

(2)

To obtain reasonable reaction rates, (solid) catalysts have to be used. Important progress was noticed in this field in the late 1960's when highly active copper-based catalysts replaced zinc-based catalysts, allowing a reduction of the process pressure from 20–30 MPa and temperatures up to about 450° C. to pressures ranging from 5–10 MPa and at considerably lower temperatures (200°–280° C.).

Methanol synthesis is a strongly exothermic ($\Delta H_{298K}=-91$ KJ/mol) equilibrium limited reaction. Both reactions (1 and 2) are exothermic (release heat) as they proceed to methanol. An increase in the temperature unfavorably influences the position of the reaction equilibrium. Moreover, the copper-based catalysts lose their activity very quickly if their maximum allowable operating temperature has been exceeded due to insufficient heat removal. As a consequence, the reactions never reach completion in the reactor. As the reaction passes through the catalyst bed, the reaction slows down and even stops, approaching an equilibrium composition based on the reactor conditions of pressure and temperature. In addition, both reactions result in a decrease in the number of moles. Thus, methanol synthesis is favored by increasing pressure and decreasing temperature, and methanol synthesis is adversely affected by decreasing pressure and rising temperature.

Two types of reactors are presently used for the commercial methanol synthesis: adiabatic bed reactors and cooled tubular reactors. An adiabatic bed reactor consists of several fixed catalyst sections or beds in series. The temperature in the beds is controlled either with heat exchangers between the beds or by introducing cold synthesis gas between the catalyst beds. In the latter or "cold-shot" construction, no heat exchangers are needed in the reactor. The main disadvantage of the cold-shot system is the dilution of the product which increases the costs of separating the product from the unconverted reactor effluent.

A cooled tubular reactor e.g. consists of a bundle of tubes filled with the catalyst. The tubes are installed in a cooling jacket and cooled e.g. by boiling water so that steam is generated from the heat generated by the reaction. This construction makes the reactor temperature easy to control. A book entitled "Methanol Production and Use", edited by the Wu-Hsun Cheng and Harold H. Kung, published by Marcel Dekker, Inc., New York, 1994, describes the typical methanol production processes on pages 51–73 and particularly describes the thermodynamics and kinetics on pages 53–61. The above pages are herein incorporated by reference.

Due to the unfavorable position of the reaction equilibrium at process temperature, the methanol concentration in the non-condensable reactor effluent is low; i.e., the methanol molar fraction usually does not exceed a value of 0.1. Therefore, the separation of the reaction product by condensation causes essential difficulties, and the heat transfer coefficients are very low such that large heat exchange areas in the condenser are required. Because of the incomplete conversion, the unconverted reactants have to be recycled to the reactor inlet by means of a compressor. The recycle ratios are commonly in the range of 5 to 10 for methanol plants. Typically the recycle ratio for a particular plant will vary according to the operating pressure, the concentration of inert compounds in the feed to the reaction, and the design approach to equilibrium.

U.S. Pat. No. 4,968,722 to Westerterp discloses a process for producing methanol by reacting carbon monoxide and hydrogen wherein these reactants in the gas phase are introduced into a reaction zone comprising one or more fixed catalyst beds and a liquid absorbent. The liquid absorbent selectively absorbs substantially all of the methanol produced. The liquid absorbent is subsequently pumped out of the reactor and flashed to recover the product methanol. In an earlier patent, U.S. Pat. No. 4,731,387, Westenerp discloses a methanol reaction zone containing a fixed bed of coarse catalyst particles having interstices between them and passing a fine particle solid adsorbent downwardly through the interstices to adsorb substantially all of the methanol product. U.S. Pat. No. 5,254,368 to Kadlec et al. discloses the integral coupling of reaction with a single-bed rapid cycle pressure swing adsorber to provide better separation and more efficient, irreversible reactions wherein the reactant is adsorbed, and those wherein the reactant is not adsorbed. Kadlec et al. describe the use of a single-bed pressure-periodic process for a two-reactant CO oxidation process for automobile pollution control. Kadlec et al. further teach a sequence of operation of the single-bed process which includes a delay step following the introduction of the feed gas and prior to an exhaust step, such that during the delay step the pressure within the single-bed adsorber is permitted to equalize as a continuous stream of product is removed.

Pressure swing adsorption (PSA) provides an efficient and economical means for separating a multi-component gas stream containing at least two gases having different adsorption characteristics. The more strongly adsorbable gas can be an impurity which is removed from the less strongly adsorbable gas which is taken off as product, or the more strongly adsorbable gas can be the desired product which is separated from the less strongly adsorbable gas. For example, it may be desired to remove impurities such as carbon monoxide and light hydrocarbons from a hydrogen-containing feed stream to produce a purified (99+%) hydrogen stream for use in a downstream catalytic process where these impurities could adversely affect the catalyst or the reaction. On the other hand, it may be desired to recover more strongly adsorbable gases, such as ethane, from a feedstream to produce an ethane-rich product.

In pressure swing adsorption, a multi-component gas stream is typically fed to at least one of a plurality of adsorption zones at an elevated pressure effective to adsorb at least one component, while at least one other component passes through. At a defined time, the feedstream to the adsorber is terminated and the adsorption zone is depressurized by one or more cocurrent depressurization steps wherein pressure is reduced to a defined level which permits the separated, less strongly adsorbed component or components remaining in the adsorption zone to be drawn off without significant concentration of the more strongly adsorbed components. Then, the adsorption zone is depressurized by a countercurrent depressurization step wherein the pressure on the adsorption zone is further reduced by withdrawing desorbed gas countercurrently to the direction of the feedstream. Finally, the adsorption zone is purged and repressurized. The combined gas stream produced during the countercurrent depressurization step and the purge step is typically referred to as the tail gas stream. The final stage of repressurization is typically performed by introducing a slipstream of product gas comprising the lightest gas component produced during the adsorption step. This final stage of repressurization is often referred to as product repressurization.

In multi-zone systems there are typically additional steps, and those noted above may be done in stages. U.S. Pat. Nos. 3,176,444 issued to Kiyonaga, 3,986,849 issued to Fuderer et al., and 3,430,418 and 3,703,068 both issued to Wagner, among others, describe multi-zone, adiabatic pressure swing adsorption systems employing both cocurrent and countercurrent depressurization. The disclosures of these patents are incorporated by reference in their entireties.

Various classes of adsorbents are known to be suitable for use in PSA systems, the selection of which is dependent upon the feedstream components and other factors generally known to those skilled in the art. In general, suitable adsorbents include molecular sieves, silica gel, activated carbon, and activated alumina. When PSA processes are used to purify hydrogen-containing streams, the hydrogen is essentially not adsorbed on the adsorbent.

A British patent application GB 2,233,329A, published Jan. 9, 1991 discloses a process for the production of methanol wherein synthesis gas is produced by steam reforming of natural gas and secondary reforming using air and wherein the synthesis gas is compressed into a conventional methanol loop comprising a first methanol synthesis reactor in which nitrogen is allowed to build up in the recycle stream. A large purge is taken from the recycle stream and passed to a second methanol synthesis reaction system containing a mixture of methanol synthesis catalyst and a methanol adsorbent wherein further methanol is produced. The second methanol synthesis reaction system operates cyclically, recovering methanol by sweeping methanol from the adsorbent with desulfurized natural gas or depressurizing. The methanol product is recovered by condensing the desorbed methanol.

Improved processes are sought for the combination of pressure swing adsorption and reaction for reversible reactions wherein non-adsorbable and less-readily adsorbable reactants react to produce adsorbable products.

Improved processes are sought for the production of methanol from synthesis gas.

Processes are sought which extend the equilibrium conversion and provide a methanol product with fewer impurities.

Processes which produce methanol have been limited by the degree to which equilibrium conversion in reversible reactions can be approached. Prior attempts to employ adsorbents and reaction have been limited by the tendency of the reactions to reverse upon depressurization or desorption of the methanol resulting in the loss of conversion and lower product purity. Processes for the production of methanol are sought which permit the production of methanol to proceed with a greater conversion per pass and with a yield of a high purity product. In addition, processes are sought which substantially reduce or eliminate the recycle of unreacted components.

SUMMARY OF THE INVENTION

Many commercial processes for the production of chemicals involve the integration of chemical reaction and separation—such as distillation, adsorption, and condensation, but not in the same zone. Conventionally, these reactions are carried out in the vapor phase at high pressure and the products of the reaction are separated at lower pressure by pressure swing adsorption techniques. For example, if the reaction involves the production of a readily-adsorbable product from at least one reactant which is non-adsorbable, the non-adsorbable reactant is separated at low pressure following the reaction and returned to the reactor. Generally the conversion of the reactant in the reactor is low, requiting large amounts of the reactant to be recompressed to the higher reaction pressure and returned to the reactor as a recycle gas. This recycle operation is costly in terms of capital and operating costs. When the reaction and the PSA process can be combined, the overall process can be improved considerably to improve the conversion of the reaction and to decrease the amount of recycle.

An example of such a system where the reactants have to be separated from the products and recycled to the reactor at significant cost is the process for methanol production from a carbon oxide and hydrogen. The reactions which produce the methanol are reversible and in equilibrium at a given combination of reactor temperature and pressure. This invention provides an improved process for the production of methanol from a synthesis gas comprising hydrogen and a carbon oxide such as carbon monoxide and carbon dioxide. By the combination of the methanol synthesis reaction within a PSA system, the conversion of the reactants to methanol and the overall process efficiency can be increased over conventional methods. In the operation of the process, the hydrogen and carbon monoxide are introduced to a fixed reactor adsorber bed at a reaction temperature and pressure. In the fixed reactor/adsorber bed, the reactants combine to produce methanol, which is simultaneously adsorbed. This allows the reaction to reach high levels of conversion. However, in order to recover the methanol product, the adsorber/reactor must be depressurized. Conventional depressurization will result in the loss of methanol product. Applicant provides a number of steps which may be used individually or together to prevent the reversal of the reaction during the desorption and product recovery steps. In addition, this combination of PSA and reaction of synthesis gas to methanol achieves a significant reduction in the amount of compression and refrigeration requirements in downstream separations to obtain the methanol product.

In one aspect the present invention relates to a process for the production of at least one readily-adsorbable product from a reaction mixture by a reversible reaction. The reaction mixture comprises a non-adsorbable reactant and a less-readily adsorbable reactant. The process comprises passing the reaction mixture at reaction conditions including a reaction temperature and a reaction pressure to a first fixed bed of at least two fixed beds of a pressure swing adsorption and reaction zone. Each of the fixed beds contains a selective adsorbent and a catalyst uniformly distributed therein. The selective adsorbent is selective for the adsorption of the readily-adsorbable product and the less-readily adsorbable reactant. The catalyst is selective for the reaction of the reactants to produce the product. The reactants are reacted to produce the product, and a first effluent stream comprising the non-adsorbable reactant is withdrawn. The passing of the reaction mixture to the first fixed bed is terminated. The first fixed bed is cocurrently purged with a first purge stream comprising the nonadsorbable reactant to provide additional conversion of the less-readily adsorbable reactant. A second effluent stream comprising the non-adsorbable reactant is withdrawn. The first fixed bed is countercurrently depressurized to a desorption pressure and desorption temperature and simultaneously purged with a second purge stream to desorb the product, and a tail gas stream comprising the product is withdrawn. The first fixed bed is repressurized to the reaction conditions and the above steps are repeated to provide a continuous process. The tail gas stream is cooled and condensed to recover a product stream.

In another aspect of the invention, a process is provided for the production of methanol from a synthesis gas stream comprising a carbon oxide and hydrogen in a pressure swing adsorption (PSA) and reaction zone. The pressure swing adsorption and reaction zone comprises at least two fixed beds. Each fixed bed contains an adsorbent selective for the adsorption of methanol and a catalyst selective for an equilibrium reaction of the synthesis gas stream to produce methanol. The process comprises passing the synthesis gas stream at a reaction temperature and a reaction pressure to the fixed bed and withdrawing an effluent stream at an adsorption pressure comprising hydrogen. The passing of the synthesis gas is terminated and the fixed bed is depressurized to a desorption pressure lower than the adsorption pressure and a product stream comprising methanol is withdrawn.

In a further embodiment, a process is provided for the production of methanol from a synthesis gas stream comprising a carbon oxide and hydrogen. The process takes place in a pressure swing adsorption (PSA) and reaction zone. The PSA and reaction zone contains a first fixed bed of at least two fixed beds. The process comprises a number of sequential steps. The synthesis gas at a reaction and reaction pressure is passed to the first fixed bed of the PSA and reaction zone. Each of the fixed beds has a feed end and an effluent end and contains an adsorbent selective for the adsorption of methanol and a catalyst selective for an equilibrium reaction of the synthesis gas to produce methanol. The adsorbent and the catalyst are uniformly distributed throughout the fixed beds. A first effluent stream comprising hydrogen is withdrawn from the first fixed bed. The passing of the synthesis gas to the first fixed bed is terminated. A purge gas stream from a second fixed bed is passed to the feed end of the first fixed bed and a second effluent stream is withdrawn. The first fixed bed is depressurized and simultaneously purged to a desorption pressure and a first product stream comprising methanol is withdrawn. The first fixed bed is repressurized and the cycle is repeated to provide a continuous process.

In a still further embodiment of the invention, a process is provided for the production of methanol from a synthesis gas stream comprising hydrogen and carbon oxide. The process comprises passing the synthesis gas stream having a molar milo of carbon to hydrogen in excess of 2.3 to a compressor to provide a compressed synthesis gas stream at a reaction pressure. The compressed synthesis gas is passed to a pressure swing adsorption (PSA) and reaction zone comprising at least one fixed bed containing an adsorbent selective for the adsorption of methanol and a catalyst for an equilibrium conversion of the synthesis gas to methanol. The catalyst and the adsorbent are uniformly distributed throughout the fixed bed. An effluent stream comprising hydrogen is recovered at about the reaction pressure from the fixed bed and a crude methanol stream comprising methanol is recovered at a desorption pressure. The crude methanol stream is passed to a methanol purification zone to provide a pure methanol stream and a recycle stream comprising carbon monoxide. At least a portion of the recycle stream is admixed with the synthesis gas stream prior to passing the synthesis gas stream to the compressor.

In a yet further embodiment of the invention, a process is provided for the production of methanol from a synthesis gas stream comprising hydrogen and carbon monoxide. The process comprises passing the synthesis gas stream having a molar ratio of carbon to hydrogen in excess of 2.3 to a secondary reforming zone and therein contacting the synthesis gas stream with an oxygen containing stream to provide a lean synthesis gas stream having about a stoichiometric ratio of carbon to hydrogen. The lean synthesis gas is passed to a compressor to provide a compressed lean gas stream at a reaction pressure. The compressed lean gas is passed to a pressure swing adsorption (PSA) and reaction zone comprising at least a first fixed bed of at least two fixed beds. Each of the fixed beds contains an adsorbent selective for the adsorption of methanol and a catalyst for an equilibrium conversion of the synthesis gas to methanol. The catalyst and the adsorbent are uniformly distributed throughout the fixed beds. An effluent stream comprising hydrogen is withdrawn at about the reaction pressure from the first fixed bed. The first fixed bed is depressurized to a desorption pressure and a crude methanol stream comprising methanol is withdrawn. The crude methanol stream is recovered and the steps of reaction and depressurization are repeated to provide a continuous process.

DETAILED DESCRIPTION OF THE INVENTION

Integration of the pressure swing adsorption separation process with a reversible chemical reaction results in a combination of two unsteady-state phenomena. By the proper combination of catalyst, adsorbent, reaction and adsorption rates, and adsorbents having varying degrees of selectivity for the reactants and products, a processing cycle can be developed to improve the conversion of the reactants compared to a conventional steady-state reaction and separation system. Reversible reaction systems—particularly those systems wherein one reaction is favored at a high pressure, and the reverse reaction is favored at a lower pressure, and where one or more of the reactants may be more-readily or less-readily adsorbable than another—are particularly preferred systems for pressure swing adsorption and reaction processes. Such systems are more preferred if the rates of reaction are similar to the rate of adsorption and desorption of the reactants and products for the range of temperatures and pressures over which the process is operated. In a simple system a feedstream comprising a non-adsorbable reactant is passed to a PSA reaction zone to produce a more-readily adsorbable product by reaction at high pressure. If an excess of reactant is present in the feedstream, an effluent stream comprising the non-adsorbable reactant will be withdrawn. Upon depressurization, the more-readily adsorbable product would be desorbed and withdrawn as a product stream. Most commercial processes are not this simple and often require at least a second, less-readily reactant adsorbable reactant to form the product of the reaction. In addition, there will be co-products, some of which will be non-adsorbable and some will be more-readily adsorbable. The nonadsorbable co-products will be withdrawn with the effluent during a reaction/adsorption step, while a more-readily adsorbable co-product will be recovered with the product and require further separation.

One important commercial reaction which can be processes in a pressure swing adsorption with reaction is the conversion of methanol from hydrogen and a carbon oxide. As noted in reactions (1) and (2) presented hereinabove, the production of methanol from synthesis gas represents an equilibrium reversible reaction wherein the product can be readily adsorbed and one of the reactants is non-adsorbable. The reaction mixture can be characterized as a combination of a non-adsorbable reactant, hydrogen, and a less-readily adsorbable component, a carbon oxide. The reaction produces a readily-adsorbed product, methanol, and a more-readily adsorbed co-product, water. In a reaction system comprising both an adsorbent selective for the adsorption of the readily-adsorbed product and the more-readily adsorbed co-product, the equilibrium reversible reaction can be made to favor the production of the product by removing the product and the co-product from the reaction zone as soon as they are produced while the non-adsorbable reactant is withdrawn. When the reaction takes place in a fixed adsorbent bed, mass transfer zones of each species of less-readily, readily-, and more-readily adsorbable components are formed within the fixed bed. As the reaction proceeds during a reaction/adsorption step, the reactant mass transfer zones lead the product mass transfer zones. Surprisingly, it was discovered that when one of the reactants is less-readily adsorbable, the conversion can be improved by the addition of a high pressure purge step following the adsorption/reaction step wherein the non-adsorbable reactant is employed to cocurrently purge the fixed bed. During the high pressure purge step, the remaining less-readily adsorbable reactant is converted to product while the non-regenerable reactant continues to be withdrawn from the bed. The non-regenerable reactant withdrawn from the bed during the adsorption/reaction step and the high pressure purge step may be used to purge another fixed bed in the process which preferably will comprise at least two beds. This technique for purging at high pressure to drive the reaction toward completion may be applied to reactions wherein the co-product is recovered with the product on depressurization or wherein the co-product is non-adsorbable and is recovered with the effluent at high pressure.

A process is disclosed for the production of methanol from a synthesis gas stream comprising hydrogen and a carbon oxide such as carbon monoxide and/or carbon dioxide as the major reactants. In the process the production of methanol is achieved by conducting the equilibrium reversible reaction and the product separation steps in a pressure swing adsorption zone containing a uniformly distributed adsorbent for the selective adsorption of methanol and a uniformly distributed catalyst for the conversion of the synthesis gas to methanol. Depending upon the type of adsorbent and the activity of the catalyst and the temperature of operation, the volumetric ratio of the adsorbent to catalyst in each bed of the pressure swing adsorption and reaction zone preferably will range from about 19:1 to about 1:19, and more preferably the volumetric ratio of adsorbent to catalyst in each bed will range from about 9:1 to about 1:9. More specifically, the process achieves the production of methanol by the reaction of hydrogen and the carbon oxide with the simultaneous adsorption of the methanol at the reaction temperature and pressure. The process may be carried out adiabatically with no heat gain or loss to the surroundings, or the process may be carried out isothermally with heat removed or added as necessary to maintain the reaction and adsorption temperatures within a limited temperature range. In the PSA and reaction process of the current invention, the synthesis gas stream is passed to the bed and an effluent stream comprising hydrogen is withdrawn. The passing of the synthesis stream to the bed is terminated prior to the breakthrough of methanol and the bed is depressurized to desorb the methanol product. In one embodiment, the bed is purged with at least a portion of the effluent stream while depressurizing the bed to a desorption pressure which is lower than the adsorption pressure.

During the adsorption/reaction step, the reaction may be exothermic and produce heat, or the reaction may be endothermic and consume heat. It is preferred to maintain the reaction temperature near isothermal conditions within the bed. Thus, provisions are made to add or remove heat from the bed as the reaction proceeds. Such provisions may include the use of heat exchange coils or tubes, or the use of a diluent such as nitrogen, methane, and mixtures thereof, in the reaction mixture to maintain the temperature change or the difference between the reaction and adsorption temperatures in the bed to less than 20° C., and preferably to maintain the temperature change in the bed to less than 15° C.

The bed may be purged and depressurized in a countercurrent manner, i.e., in a direction opposite to the flow of the synthesis gas during the previous adsorption/reaction step, wherein the purge gas is introduced at the effluent end of the bed and the desorbed bed methanol is recovered from the feed end of the bed. The bed may be purged and depressurized in a cocurrent manner, i.e., in the same direction and the adsorption/reaction step, wherein the purge stream is introduced at the feed end of the bed and the methane is withdrawn from the effluent end of the bed. The methanol synthesis reaction in this case requires a stoichiometric excess of hydrogen relative to the carbon oxide in the synthesis gas. The carbon oxide may be carbon monoxide or carbon dioxide. Preferably, the ratio of hydrogen to carbon monoxide will be between about 2.0 to about 5.0 and more preferably, the ratio of hydrogen to carbon monoxide will range from about 2.0 to about 3.0. Other compounds such as nitrogen, carbon dioxide, methane, and mixtures thereof also may be present in the synthesis gas. The reaction and adsorption conditions in the pressure swing adsorption and reaction zone will range from a reaction temperature from about 100° C. to about 350° C., and preferably will range from about 175° C. to about 300° C. The reaction may be carded out over a wide range of pressure which retains the reactants and products in the vapor state, preferably, the reaction pressure will range from about 1 MPa to about 20 MPa.

The catalyst employed in the methanol synthesis reaction is based on a copper oxide-zinc oxide-alumina catalyst. Well-known catalysts in the copper-zinc-alumina family typically have a formulation within the following range:

Copper oxide 60–70%

Zinc oxide 20–30%

Alumina 5–15%

Typically these catalyst are supplied in oxide form and are reduced insitu by passing over the catalyst bed a controlled amount of hydrogen (around 1 mol%) in a carrier gas, such as nitrogen or methane at temperatures typically less than 280° C. to activate the catalyst. Preferably the catalyst will be prepared in a tablet or bead form.

Generally, the copper-oxide based catalysts are particularly sensitive to sulfur and chlorine, which may permanently deactivate the catalyst. Therefore, the feed gas, such as natural gas and liquified petroleum gas (LPG), to a methanol plant employing a copper-oxide catalyst is treated to remove sulfur as $H_2S$ to levels below 0.1 ppm vol. which results in a synthesis gas containing less than 0.025 ppm-vol sulfur. This sulfur removal is generally accomplished with a guard bed system containing cobalt oxidemolybdenum oxide/zinc oxide sorbent. Chlorine when present in the feed gas must also be removed by a guard bed system containing specially formulated chlorine guard sorbents well-known to those skilled in the art. In the pressure swing adsorption and reaction zone, the catalyst will be intermixed with the adsorbent selective for the adsorption of methanol. Although the catalyst may be placed anywhere in the fixed beds of the PSA zone, such as the feed end of the bed, in the center of the bed, and at the effluent end of the bed, it is preferred that the catalyst be uniformly distributed throughout the beds of the PSA zone.

In a further embodiment, the pressure swing adsorption and reaction zone is employed in a methanol synthesis loop wherein the synthesis gas stream has a molar ratio of carbon to hydrogen in excess of 2.3. A crude methanol stream is withdrawn from the PSA and reaction zone and passed to a methanol purification zone to provide a pure methanol stream and a recycle stream. At least a portion of the recycle stream is admixed with the synthesis gas stream. In a still further embodiment, the synthesis gas stream having a molar ratio of carbon to hydrogen in excess of about 2.3 is passed to a secondary reforming zone to provide a lean synthesis gas stream having about a stoichiometric ratio of carbon to hydrogen. The lean synthesis gas stream is compressed to a reaction pressure and the compressed lean gas stream is passed to a pressure swing and reaction zone containing an adsorbent for the adsorption of methanol and a catalyst for the production of methanol. The use of the pressure swing adsorption and reaction zone results in a higher conversion of the synthesis gas to methanol and significantly reduces the capital and operation costs in the production of methanol. Furthermore, the simultaneous reaction and adsorption of methanol minimizes the production of by-products such as ethers, including dimethylether, aldehydes, esters, and ketones, ethanol, water, and higher alcohols. If nitrogen is present in the synthesis gas, trace amounts of amines may be formed.

The pressure swing adsorption process is an essentially adiabatic process for separating a multi-component fluid containing at least one selectively adsorbable component. The PSA process of the invention relates to conventional PSA processing in which each bed of an adsorption zone undergoes, on a cyclic basis, high pressure adsorption, optional cocurrent depressurization to intermediate pressure level(s) with release of void space gas from the effluent end of the bed, depressurization to lower desorption pressure with the release of desorbed gas from the feed end of the bed, with or without purge of the bed, and repressurization to higher adsorption pressure. The adsorption zone is then countercurrently or cocurrently depressurized to a desorption pressure that is at or above atmospheric pressure with the more adsorbable component(s) being discharged from the feed end thereof as a product. In the multibed adsorption systems to which the invention is directed, the displacement or purge gas used for each bed is obtained by diverting a portion of the gas released from that or another bed in the system during the adsorption steps. Repressurization of the bed is obtained by introducing a portion of the purge gas or by introducing the synthesis gas at the adsorption pressure.

Those skilled in the art will appreciate that the high pressure adsorption step of the PSA process comprises introducing the PSA feedstream to the feed end of the adsorbent bed at a high adsorption pressure. The less readily adsorbable component(s) passes through the bed and is discharged from the effluent or produce end thereof. Adsorption fronts comprising the more adsorbable component(s) are established in the bed with the fronts likewise moving through the bed from the feed end toward the product end thereof. When the feedstream contains a less readily adsorbable component and a more readily adsorbable component, a leading adsorption front of the more readily adsorbable component will be established and will move through the bed in the direction of the product or discharge end thereof.

It will further be understood that various changes and modifications can be made in the details of the PSA zone as herein described and illustrated above without departing from the scope of the invention as set forth in the appended claims. In addition the number of beds employed may be varied depending upon the circumstances and results desired in any given application. Accordingly, the individual PSA steps described, as well as conventional variations thereof, are generally known by those skilled in the an and need not be further described herein. It will be further understood that PSA systems necessarily incorporate various conduits, valves, and other control features to accomplish the necessary switching of adsorbent beds from one step to the next, in appropriate sequence as in conventional PSA operations.

It will also be understood that the invention can be carried out using any suitable adsorbent material in the adsorption zone having a selectivity for various components of a feedstream over other such components, thereby providing a less readily adsorbable component and a more readily adsorbable component. Suitable adsorbents known in the an and commercially available include crystalline molecular sieves, activated carbons, activated clays, silica gels, activated aluminas and the like. The molecular sieves include, for example, the various forms of silicoaluminophosphates and aluminophosphates disclosed in U.S. Pat. Nos. 4,440,871; 4,310,440 and 4,567,027, hereby incorporated by reference, as well as zeolitic molecular sieves. Preferably, the solid adsorbent selective for the adsorption of methanol is selected from the group consisting of silica gel, activated carbon, activated alumina, zeolite molecular sieves, and mixtures thereof.

Zeolitic molecular sieves in the calcined form may be represented by the general formula;

$$Me_{2/n}O: Al_2O_3: xSiO_2: yH_2O$$

where Me is a cation, x has a value from about 2 to infinity, n is the cation valence and y has a value of from about 2 to 10.

Typical well-known zeolites which may be used include chabazite (also referred to as Zeolite D), clinoptilolite, erionite, faujasite (also referred to as Zeolite X and Zeolite Y), ferrierite, mordenite, Zeolite A, and Zeolite P. Other zeolites suitable for use according to the present invention are those having a high silica content, i.e., those having silica to alumina ratios greater than 10 and typically greater than 100. Detailed descriptions of some of the above identified zeolites may be found in D. W. Breck, *ZEOLITE MOLECULAR SIEVES*, John Wiley and Sons, New York, 1974, hereby incorporated by reference.

It is often desirable when using crystalline molecular sieves that the molecular sieve be agglomerated with a binder in order to ensure that the adsorbent will have suitable physical properties. Although there are a variety of synthetic and naturally occurring binder materials available such as metal oxides, clays, silicas, aluminas, silica-aluminas, silica-zirconias, silica-thorias, silica-berylias, silica-titanias, silica-alumina-thorias, silica-alumina-zirconias, mixtures of these and the like, claytype binders are preferred. Examples of clays which may be employed to agglomerate the molecular sieve without substantially altering the adsorptive properties of the zeolite are attapulgite, kaolin, volclay, sepiolite, palygorskite, kaolinitc, bentonitc, montmorillonite, illite, and chlorite. The choice of a suitable binder and of methods employed to agglomerate the molecular sieves is generally known to those skilled in the an and need not be further described herein.

The process of the present invention is hereinafter described with reference to the drawings which illustrate various aspects of the present invention. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation column overhead and reboiler systems, etc. It may also be readily discerned that the process flow presented in the drawings may be modified in many aspects without departing from the basic overall concept of the invention. For example, the number of heat exchangers shown in the drawings have been held to a minimum for purposes of simplicity. Those skilled in the art will recognize that the choice of heat exchange methods employed to obtain the necessary heating and cooling at various points within the process is subject to a large amount of variation as to how it is performed. Accordingly, there exists many possibilities for indirect heat exchange between different process streams. Depending on the specific location and circumstance of the installation of the subject process, it may also be desired to employ heat exchange against steam, hot oil, or process streams from other processing units not shown on the drawings.

Figure 1:
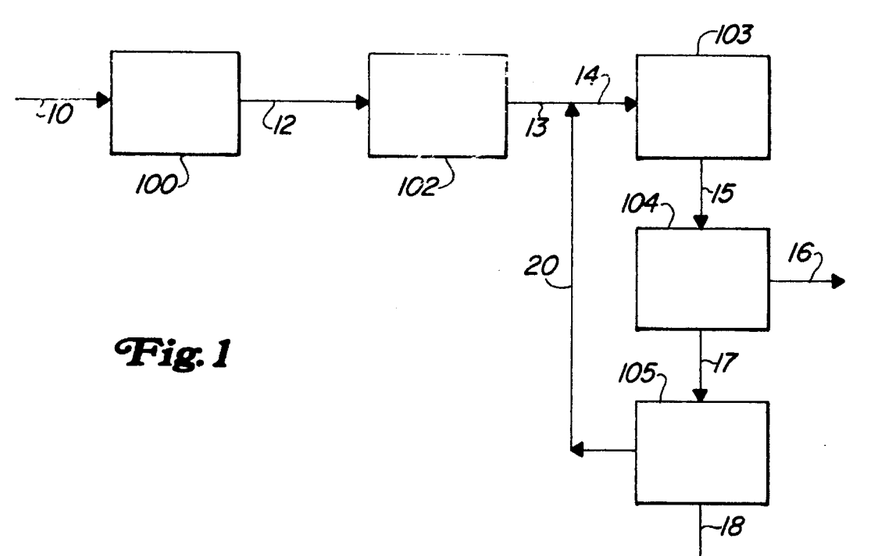
FIG. 1 is a schematic flow diagram of the process of the present invention for the production of methanol with a primary synthesis gas reaction zone.

FIG. 1 illustrates a process flowscheme that can be employed for the production of methanol from natural gas using one steam-reforming stage. The natural gas feedstream 10 comprising methane and carbon monoxide is passed to a desulfurization zone 100 to remove sulfur impurities. Typically, the natural gas feedstream contains from about 300 ppm-wt to about 3 wt-% sulfur compounds including hydrogen sulfide, mercaptan sulfur, carbon disulfide, and mixtures thereof. The desulfurization may be accomplished by sorption techniques over a fixed bed of solid sorbent such as zinc oxide to provide a desulfurized gas stream in line 12. The desulfurized gas stream 12 is passed to the steam-reforming zone 102 at a sufficient temperature and pressure and in the presence of a metal oxide catalyst such that the methane reacts with water to produce carbon monoxide and hydrogen, and carbon monoxide will react with water to produce carbon dioxide and hydrogen according to the following equations:

$$CH_4 + H_2O \rightleftharpoons CO + 3H_2$$

$$CO + H_2O \rightleftharpoons CO_2 + 3H_2$$

A synthesis gas stream 13 comprising hydrogen, carbon monoxide, and carbon dioxide is withdrawn from the steam-reforming zone 102 and is combined with a recycle stream 20 in line 14 and a combined synthesis gas stream 14 is passed to a compressor 103. The compressor raises the synthesis gas stream from a pressure of about 0.5 kPa to 8.0 MPa to a synthesis reaction pressure. The synthesis reaction pressure, preferably will range from about 0.5 MPa to about 20 MPa, and more preferably will range from about 5 MPa to about 10 MPa. The compressed synthesis gas is withdrawn from the compressor 103 and passed via line 15 to a pressure swing adsorption and reaction zone 104. In the pressure swing adsorption PSA and reaction zone 104, the methanol synthesis equilibrium reactions occur at a reaction temperature ranging from about 175° C. to about 300° C.

and a reaction pressure ranging from about 0.5 MPa to about 20 MPa. The pressure swing adsorption zone and reaction zone 104 comprises at least 2 fixed beds containing a methanol synthesis catalyst and an adsorbent selective for the adsorption of methanol. A hydrogen stream 16 is withdrawn from the PSA and reaction zone 104 at the reaction conditions. At least a portion of the hydrogen stream 16 is employed to purge another of the fixed beds following an adsorption reaction step to prevent a reversal of the methanol synthesis reactions. The passing of the compressed synthesis gas stream is terminated prior to breakthrough of either oxide carbon or methanol. Following the reaction/adsorption step, the fixed bed is purged at high pressure in a cocurrent direction (relative to the direction of the flow of compressed synthesis gas during the adsorption/reaction step) and a second hydrogen stream is recovered. This high pressure purge supplies additional hydrogen to the adsorption/reaction zone to convert at least a portion of the remaining carbon dioxide or carbon monoxide in the fixed bed. The high pressure purge is terminated and a countercurrent depressurization is performed to provide a tail gas stream 17 comprising methanol. Preferably, a portion of the hydrogen stream 16 is employed to simultaneously countercurrently purge the fixed bed during the countercurrent depressurization step to prevent the reversal of the synthesis gas reaction as pressure is reduced. The tail gas stream 17 is withdrawn from the PSA and reaction zone 104 and passed to a separation zone 105 wherein the tail gas 17 is separated into a crude methanol product 18 and the recycle stream 20. Optionally, following the high pressure purge, the fixed bed may be cocurrently depressurized and purged to provide the tail gas stream from the effluent end of the fixed bed.

Figure 2:
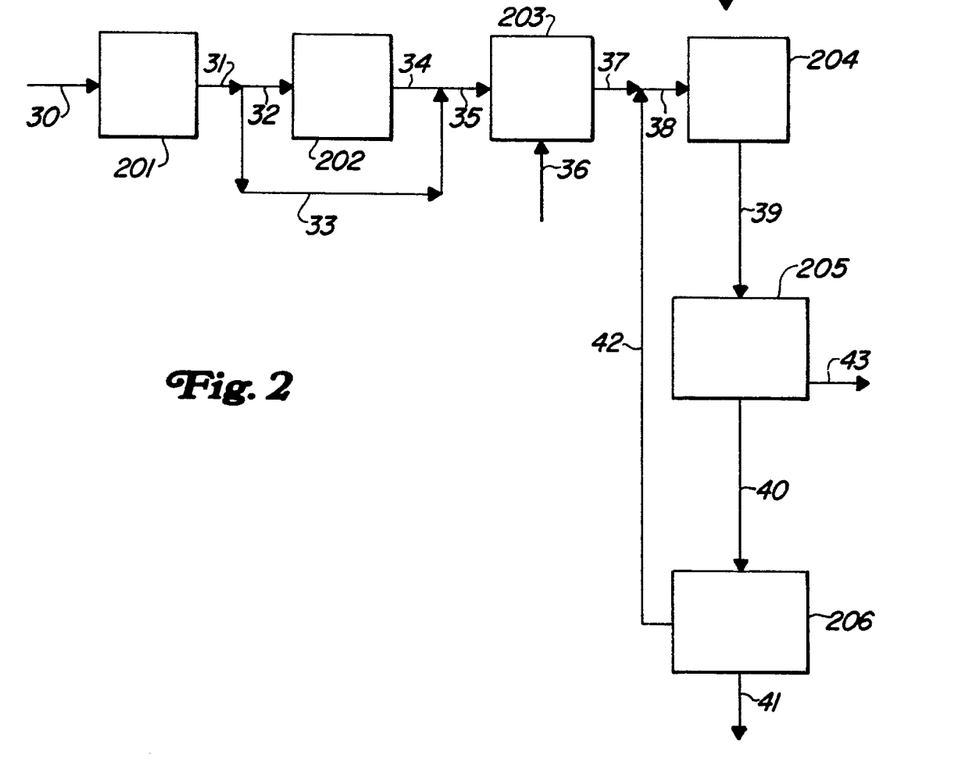
FIG. 2 is a schematic flow diagram of the process of the present invention for the production of methanol with the addition of a secondary synthesis gas reaction zone.

FIG. 2 illustrates to a process flowscheme for the production of methanol from natural gas using a secondary reforming step. The secondary reforming step refers to the further oxidizing of unconverted methane in the effluent from the steam-reforming process to provide carbon monoxide and hydrogen when oxygen is employed as the oxidation agent, according to the reaction:

$$CH_4 + 0.5\ O_2 \leftrightharpoons CO + 2H_2$$

The secondary reforming reaction takes place over a nickel catalyst and is well-known to those skilled in the art of methanol production. Referring to FIG. 2, a natural gas stream 30 is passed to a desulfurization zone 201 to remove sulfur compounds and provide a desulfurized natural gas stream in line 31. A portion of the desulfurized natural gas stream is passed via line 32 to a primary reforming zone 202 wherein the desulfurized natural gas stream 32 is heated and combined with steam and passed over a copper-based catalyst. In the primary reforming zone hydrocarbons react with the water to produce a mixture of carbon monoxide, carbon dioxide, and hydrogen herein called primary synthesis gas 34. The primary synthesis gas in line 34 may be combined with another portion of the desulfurized natural gas in line 33 and the combined gas stream 35 is passed to a secondary reforming zone 203. In the secondary reforming zone 203, an oxygen-containing stream 36 is combined with steam and the combined gas stream to provide controlled combustion of the remaining hydrocarbons over a nickel catalyst resulting in synthesis gas stream 37. A high concentration of carbon monoxide is required to produce methanol in the synthesis reaction. Preferably, the concentration of CO in the synthesis gas will range from about 10% to 20 Mol-%, and the concentration of hydrogen will range from about 20 to about 75 Mol-%. Preferably, the ratio of hydrogen to carbon monoxide in the synthesis gas stream will range from about 2 to 1, to about 5 to 1, and more preferably the ratio of hydrogen to carbon monoxide will range from about 2:1 to about 3:1. The synthesis gas stream 37 is admixed with a recycle stream 42 and the mixed synthesis gas stream 38 is passed to compressor 204. Compressor 204 raises the pressure of the compressed synthesis gas stream 39 to a pressure ranging from about 0.5 MPa to about 20 MPa. The compressed synthesis gas stream 39 at a reaction temperature and a reaction pressure is passed to a pressure swing adsorption and reaction zone 205, wherein the synthesis gas stream 38 is convened to methanol as described herein above. The pressure swing adsorption and reaction zone 205 comprises at least 2 fixed beds containing a catalyst for the production of methanol and an adsorbent selective for the adsorption of methanol. Methanol produced in the synthesis reaction is adsorbed in an adsorption/reaction step while withdrawing a hydrogen stream 43. At least a portion of the hydrogen stream is employed to purge another fixed bed undergoing desorption and depressurization steps. The adsorption/reaction step is terminated prior to breakthrough of methanol and the fixed bed is cocurrently purged at high pressure to further convert unreacted carbon monoxide and carbon dioxide. Upon termination of the high pressure purge step, the fixed bed is countercurrently depressufized and purged to provide a tail gas stream 40 comprising methanol. The tail gas stream is passed to a separation zone 206 wherein a crude methanol product is recovered in line 41 and a vapor stream comprising carbon monoxide and hydrogen is returned as recycle stream 42 to be combined with the secondary synthesis gas stream in line 37.

Generally, crude methanol produced from the methanol synthesis reaction is refined to pure methanol product by distillation. The number of impurities and the concentration of these by-products depends on the methanol synthesis conditions and the composition of the gas in the synthesis loop. By the immediate adsorption of the methanol as it is produced, the production of these by-products is minimized, reducing the methanol purification costs.

In another embodiment, the oxidizing stream 36 may be air, and the nitrogen recovered from the secondary reformer 203 subsequently is recovered as the adsorber effluent in line 43 from the pressure swing adsorption and reaction zone 205.

The following examples are provided to illustrate the present invention and are not intended to limit the scope of the claims that follow.

EXAMPLE I

Figure 3:
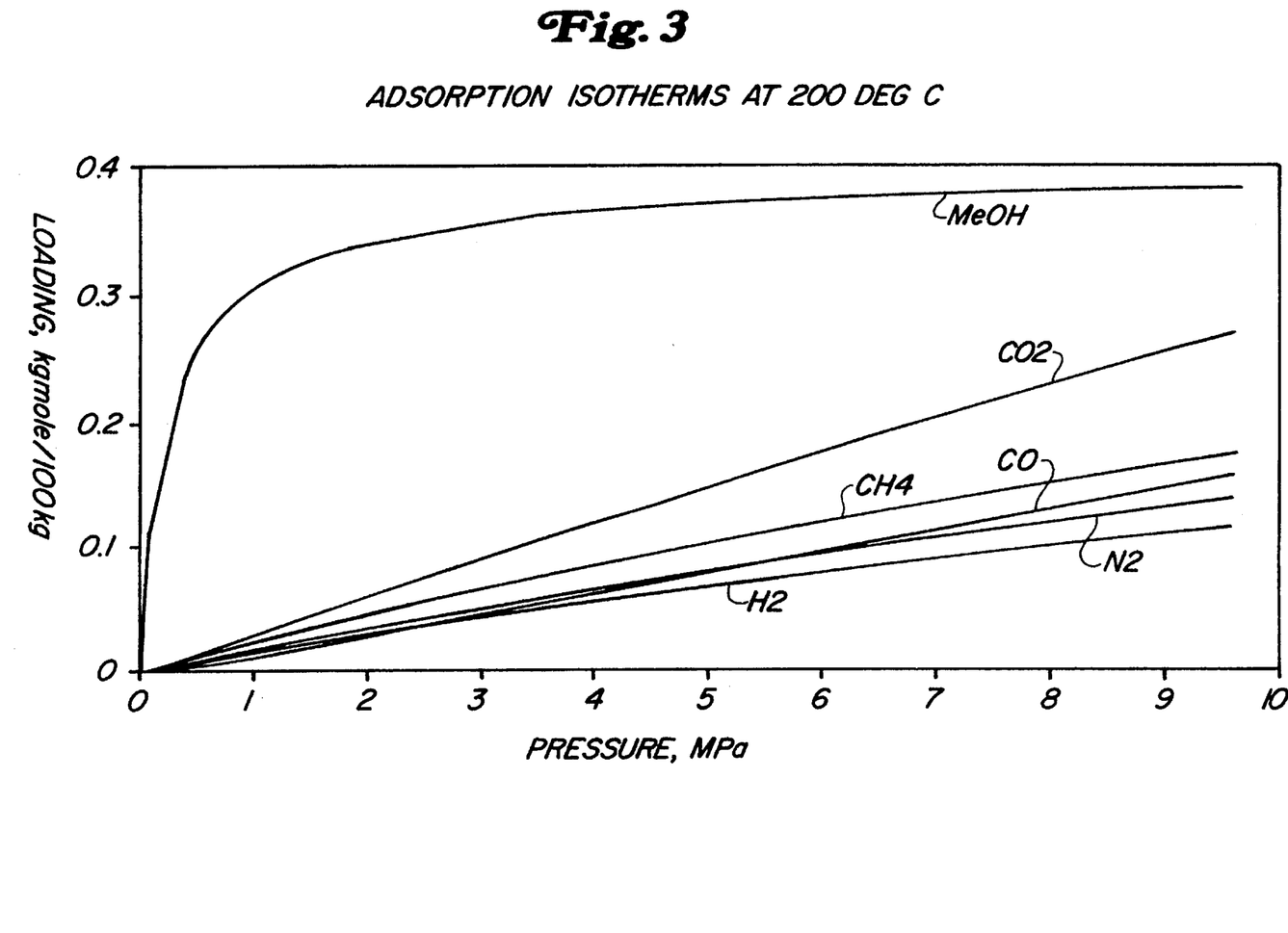
FIG. 3 is an adsorbent isotherm chart showing the relative loadings of reactants and methanol on silica gel at reaction temperature over a range of pressure.

FIG. 3 illustrates the relative adsorbent loadings for compounds which are either reactants or products of the methanol synthesis reactions at a reaction temperature of 200° C. The adsorbent loading isotherms were extrapolated from isotherm data for each component at room temperature and at least one elevated temperature using the Clauses-Clapeyron Equation, a procedure well-known to those skilled in the art of adsorption. Adsorption isotherms over silica gel are shown for hydrogen, nitrogen, carbon monoxide, methane, carbon dioxide, and methanol over a range of pressure from vacuum conditions of about 7 kPa to about 10 MPa (100 atm). The projected isotherm data indicate that silica gel will selectively adsorb methanol over the major reactants, hydrogen and carbon monoxide which will be adsorbed to lesser extent.

EXAMPLE II

Based on the adsorbent isotherm data of Example I, an engineering and mathematical simulation of the pressure swing adsorption and reaction process of the present invention was developed. A synthesis gas feed comprising hydrogen and carbon monoxide in a 3:1 molar ratio at a temperature of 100° C. and a pressure of about 50 atm was charged to a fixed bed adsorber/reactor and a first adsorption effluent comprising hydrogen was withdrawn. The reactor bed contained equal volume amounts of a copper-oxide/zinc oxide/alumina catalyst and silica gel adsorbent uniformly distributed within the reactor bed. The temperature of the fixed bed was maintained at a reaction temperature of about 200° C. by the removal of the heat of reaction. This adsorption/reaction step was continued for about 50 seconds. Following the adsorption/reaction step, the fixed bed was purged at a pressure of 50 atm with a purge gas comprising hydrogen for a period of about 50 seconds during which time a second adsorption effluent comprising hydrogen was withdrawn. The fixed bed was then countercurrently purged, i.e., in a direction countercurrent to the introduction of the synthesis gas in the adsorption/reaction step, and the fixed bed was simultaneously depressurized to a desorption pressure of about 10 atm, over a period of about 400 seconds. During the countercurrent purge step, a purge stream comprising hydrogen at a temperature of about 200° C. was introduced at the effluent end of the fixed bed and a tail gas, or desorption stream, comprising methanol was withdrawn from the feed end of the fixed bed. Following the countercurrent purge and depressurization step, the fixed bed was repressurized with a hydrogen stream at a temperature of 200° C. and a pressure of about 50 atm over a period of about 100 seconds. The cycle of adsorption/reaction, high pressure purge, countercurrent purge/depressurization, and repressurization was continued to provide a continuous process. Methanol was recovered in the tail gas at a conversion based on the reaction of carbon monoxide in the feed gas at a level of about 75.8%.

EXAMPLE III

To further assess the advantage of the purge prior to depressurization, a simulation was developed along the lines of Example II. A synthesis gas stream comprising hydrogen and carbon monoxide and having a molar ratio of 3:1 hydrogen to carbon monoxide was charged to a fixed bed adsorber/reactor. The process of Example II was followed, except no hydrogen purge was made at high pressure between the adsorption/reaction step and the purge/depressurization step, and the adsorption/reaction time was increased to about 100 seconds. The steps of the process consisted of adsorption/reaction, purge/depressurization, and repressurization. These steps were repeated to provide a continuous process. After the completion of about 5 cycles, the methanol conversion had reached a stable level of 63.6%. Thus, the relative methane conversion results of Example II represent an improvement of about 20% over the case of Example III when no purge was employed prior to depressurization. The depressurization step included a simultaneous purge in the countercurrent direction.

EXAMPLE IV

Based on Example III, an evaluation was made to assess the rate of depressurization on the conversion of carbon monoxide to methanol. Depressurization times of 25, 50, and 100 seconds were employed without the simultaneous purge during depressurization from about 50 atm to about 10 atm. At a depressurization time of 25 seconds, the conversion to methanol was about 63.6%. When the purge time was extended to 50 seconds, the conversion to methanol dropped to about 48.7%, a 23 percent reduction. Thus, there was a benefit to employing a depressurization time which is shorter than the adsorption/reaction time and preferably the depressurization time takes place as rapidly as possible.

EXAMPLE V

A further extension of the process steps followed in Example II was simulated with the adsorption/reaction time extended to about 200 seconds and the depressurization was conducted without a high pressure hydrogen purge. After the completion of 5 cycles, the quasi steady-state methanol conversion reached in the fixed bed was 47.3 percent. The lower conversion for this case is due in part to the breakthrough of methanol, exceeding the capacity of the adsorbent and resulting in the loss of methanol. It is believed that this drop in conversion further suggests that the reaction has shifted away from methanol and that some loss of methanol occurred during depressurization.

EXAMPLE VI

A series of simulations based on the process of Example II and Example III were made to establish the effect of employing a hydrogen purge during depressurization, and the effect of the direction of the depressurization relative to the direction of the flow of synthesis gas to the adsorber/reactor bed. Table 1 summarizes the results of the parametric study.

TABLE 1

EFFECT OF EMPLOYING HYDROGEN DURING DEPRESSURIZATION AND REPRESSURIZATION

| RUN | REPRES-SURIZATION | DEPRES-SURIZATION | CON-VERSION |
|---|---|---|---|
| A | $H_2$-Countercurrent | $H_2$-Countercurrent | 63.4 |
| B | $H_2$-Countercurrent | No $H_2$-Countercurrent | 27.4 |
| C | Feed-Cocurrent | $H_2$-Countercurrent | 50.5 |
| D | $H_2$ Countercurrent | $H_2$-Cocurrent | 70.4 |

For all the runs in Table 1, the adsorption/reaction step time was 100 seconds and the depressurization time was 400 seconds. In run A, the depressurization step was conducted in a counter current direction and the repressurization step with a simultaneous hydrogen purge was in a counter current direction relative to the reaction adsorption step. The conversion for run A was 63.4% based on the conversion of carbon monoxide in the synthesis gas. In run B, without the hydrogen purge, the conversion reached the lowest level in the series at 27.4%. In run C, the hydrogen purge of run A was restored, but the fixed bed was repressurized with the synthesis gas feed in a cocurrent direction. The results of run C suggest that feed repressurization is less efficient than repressurization with hydrogen. Run D employed cocurrent depressurization with a simultaneous hydrogen purge and countercurrent hydrogen repressurization. Run D resulted in a CO conversion of 70.4%, the highest conversion of the series.

EXAMPLE VII

A series of engineering simulations were developed to evaluate the usefulness of the PSA and reaction process in a complex for the production of methanol from natural gas. Table 2 provides a summary of the results of this evaluation. Each case in the series was based on an equal amount of synthesis gas feed to each methanol loop which in the conventional case, C-4, is sufficient to produce 2500 tons per day of methanol. In Run C-1, a natural gas stream was charged at a temperature of about 40° C. and a pressure of about 1 MPa to a desulfurization zone as shown in FIG. 1. As in Example II, equal volumes of adsorbent and catalyst for the production of methanol were uniformly distributed in the pressure swing adsorption and reaction zone. The desulfurized natural gas was then charged with steam to a steam-reforming zone to provide a synthesis gas. The synthesis gas compressed and heated to reaction conditions; a reaction pressure of about 50 atm and a temperature of about 200° C. The compressed synthesis gas was passed to a PSA and reaction zone to provide an adsorption effluent comprising hydrogen and a tail gas comprising methanol. The tail gas was passed to a separation zone to recover a crude methanol product and a recycle gas stream. The recycle gas stream was combined with the synthesis gas prior to compression to reaction conditions. In run C-2, a secondary reforming step was added to the C-1 scheme as shown in FIG. 2. An oxygen stream was charged to the recovery reforming zone to facilitate the further conversion of methane to carbon monoxide and hydrogen. In run C-2, it was found that the net production of hydrogen could be eliminated while further reducing the amount of recycle returned to the compressor. In run C-3, an air stream was employed at the oxygen-containing stream in the secondary reforming zone, introducing nitrogen to the synthesis gas stream. In the PSA and reaction zone, the nitrogen is recovered to be vented to the atmosphere or to be employed in other downstream processes. Runs C-1, C-2, and C-3 showed significant relative conversion advantages in excess of 2.3 times the conventional processing route in case C-4. In addition, all of the alternative cases using PSA and reaction process showed significant compression utility savings at the reduced recycle rates and higher conversion levels obtained by the process of the present invention.

TABLE 2

COMMERCIAL METHANOL PRODUCTION SCHEMES
FOR PRODUCING METHANOL

| RUN | SCHEME | RELATIVE COMPRESSION UTILITY REQUIREMENTS | RELATIVE CONVERSION |
|---|---|---|---|
| C-1 | PRIMARY REFORMING | 0.95 | 2.33 |
| C-2 | SECONDARY REFORMING WITH OXYGEN | 0.82 | 2.33 |
| C-3 | SECONDARY REFORMING WITH AIR | 0.72 | 2.33 |
| C-4 | CONVENTIONAL PRIMARY REFORMING | 1.0 | 1.0 |

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A process for the production of a methanol product by a reversible reaction of a reaction mixture comprising hydrogen and a less-readily adsorbable reactant comprising a carbon oxide, said process comprising:

a) passing said reaction mixture at reaction conditions including a reaction pressure and a reaction temperature to a first fixed bed of at least two fixed beds of a pressure swing adsorption and reaction zone, each of said fixed beds containing a selective adsorbent for the adsorption of said methanol product and said less-readily adsorbable reactant, and said first fixed bed containing a catalyst selective for the reaction of said reactants to produce said methanol product, reacting said reactants to produce said methanol product and withdrawing a first effluent stream comprising said hydrogen;

b) terminating the passing of said reaction mixture to said first bed and cocurrently purging said first fixed bed with a first purge stream comprising said hydrogen to provide additional conversion of said less-readily adsorbable reactant and withdrawing a second effluent stream comprising said hydrogen;

c) countercurrently depressurizing and simultaneously purging said first fixed bed with a second purge stream to a desorption pressure and desorption temperature to desorb said methanol product and withdrawing a tail gas stream comprising said methanol product;

d) repressurizing said first fixed bed to said reaction conditions and e) cooling and condensing said tail gas to recover a methanol product stream and repeating steps (a) to (d) to provide a continuous process.

2. The process of claim 1 further comprising simultaneously cooling said first bed during step (a) when said reversible reaction to produce said product is exothermic to maintain a reaction temperature.

3. The process of claim 1 wherein said first and second purge streams comprise at least a portion of said first and second effluent streams from another bed.

4. The process of claim 3 wherein said less-readily adsorbable reactant comprises carbon monoxide.

5. The process of claim 1 wherein said reaction is carried out in the presence of a diluent.

6. The process of claim 5 wherein said diluent comprises nitrogen.

7. The process of claim 1 wherein said selective adsorbent and said catalyst are uniformly distributed within said beds.

8. The process of claim 1 wherein said reversible reaction produces a more-adsorbable co-product.

9. The process of claim 8 wherein said tail gas stream comprises said first product and said co-product.

10. The process of claim 9 wherein said first product comprises methanol and said co-product comprises water.

11. The process of claim 10 further comprising separating said first product from said co-product to produce a purified product.

12. The process of claim 1 wherein said reversible reaction produces a non-adsorbable co-product.

13. The process of claim 12 wherein the non-adsorbable co-product is recovered in the first effluent stream.

14. A process for the production of methanol from a synthesis gas stream comprising a carbon oxide and hydrogen in a pressure swing adsorption and reaction zone, said pressure swing adsorption and reaction zone comprising at least one fixed bed, each fixed bed containing an adsorbent selective for the adsorption of methanol and a catalyst selective for an equilibrium reaction of said synthesis gas stream to produce methanol, said catalyst and said adsorbent being uniformly distributed throughout said fixed bed, said process comprising passing said synthesis gas stream at a reaction temperature and reaction pressure to said fixed bed and withdrawing an effluent stream at an adsorption pressure, said effluent stream comprising hydrogen, depressurizing said fixed bed to a desorption pressure lower than said adsorption pressure, and withdrawing a product stream comprising methanol.

15. The process of claim 14 wherein the hydrogen and carbon monoxide are present in a stoichiometric ratio ranging from about 2 to about 3.

16. The process of claim 14 wherein the reaction temperature ranges from about 175° C. to about 300° C.

17. The process of claim 14 wherein the reaction pressure ranges from about 0.5 MPa to about 20 MPa.

18. The process of claim 14 wherein said desorption pressure lower than said adsorption pressure ranges from about 0.1 MPa to about 5 MPa.

19. The process of claim 14 wherein methanol is withdrawn at a conversion rate greater than 50 mole percent.

20. The process of claim 19 wherein the selective adsorbent and the catalyst are present in a volume ratio of adsorbent to catalyst ranging from about 19:1 to about 1:19.

21. The process of claim 14 wherein the reaction pressure is about equal to said adsorption pressure.

22. The process of claim 14 further comprising terminating said passing of said synthesis gas stream to said bed and cocurrently passing at least a portion of said effluent stream to said bed prior to depressurizing said bed.

23. A process for the production of methanol from a synthesis gas stream comprising a carbon oxide and hydrogen in a pressure swing adsorption and reaction zone containing a first fixed bed of at least two fixed beds, said process comprising the following steps:
  a) passing said synthesis gas stream at a reaction temperature and reaction pressure to the first fixed bed of at least two fixed beds of said pressure swing adsorption and reaction zone, each of said fixed beds having a feed end and an effluent end and containing an adsorbent selective for the adsorption of methanol and a catalyst selective for an equilibrium reaction of said synthesis gas to produce methanol, said adsorbent and said catalyst being uniformly distributed throughout said fixed beds and withdrawing a first effluent stream comprising hydrogen from said first fixed bed;
  b) terminating said passing of said synthesis gas to said first fixed bed and passing a co-purge stream from a second fixed bed to the feed end of said first fixed bed and withdrawing a second effluent stream;
  c) depressurizing and simultaneously purging said first fixed bed to desorption pressure and withdrawing a first product stream comprising methanol; and
  d) repressurizing said first fixed bed and repeating steps (a) through (d) to provide a continuous process.

24. The process of claim 23 wherein said depressurizing is carried out in a direction cocurrent to the passing of said synthesis gas stream.

25. The process of claim 23 wherein said depressurizing is carried out in a direction which is countercurrent to the passing of said synthesis gas stream.

26. The process of claim 23 wherein the passing of said synthesis gas stream is terminated prior to the breakthrough of methanol from the first fixed bed.

27. The process of claim 23 further comprising countercurrently purging said first fixed bed prior to the repressurizing of step (d).

28. The process of claim 23 wherein said repressurizing is performed with at least a portion of said first effluent stream from said second fixed bed.

29. The process of claim 23 wherein said repressurizing is performed with at least a portion of said synthesis gas stream.

30. The process of claim 23 wherein said synthesis gas stream comprises a diluent selected from the group consisting of nitrogen, methane, and mixtures thereof.

31. The process of claim 23 further comprising removing heat from said first fixed bed to maintain a temperature change within said first fixed bed to less than 15° C.

32. A process for the production of methanol from a synthesis gas stream comprising hydrogen and carbon oxide, said process comprising:
  a) passing said synthesis gas stream having a molar ratio of carbon to hydrogen in excess of 2.3 to a compressor to provide a compressed synthesis gas stream at a reaction pressure;
  b) passing said compressed synthesis gas stream to a pressure swing adsorption and reaction zone comprising at least one fixed bed containing an adsorbent selective for the adsorption of methanol and a catalyst for the equilibrium conversion of said synthesis gas to methanol, said catalyst and said adsorbent being uniformly distributed throughout said fixed bed, and recovering an effluent stream at about said reaction pressure comprising hydrogen and depressurizing said fixed bed to a desorption pressure and recovering a crude methanol stream comprising methanol;
  c) passing said crude methanol stream to a methanol purification zone to provide a pure methanol stream and a recycle stream comprising carbon monoxide; and
  d) admixing at least a portion of said recycle stream with said synthesis gas stream prior to passing said synthesis gas stream to said compressor.

33. A process for the production of methanol from a synthesis gas stream comprising hydrogen and carbon monoxide, said process comprising:
  a) passing said synthesis gas stream having a molar ratio of carbon to hydrogen in excess of about 2.3 to a secondary reforming zone and therein contacting said synthesis gas stream with an oxygen containing stream to provide a lean synthesis gas stream having about a stoichiometric ratio of carbon to hydrogen;
  b) passing said lean synthesis gas stream to a compressor to provide a compressed lean gas stream at a reaction pressure;
  c) passing said compressed lean gas stream to a pressure swing adsorption and reaction zone comprising a first fixed bed of at least two fixed beds, each of said beds containing an adsorbent selective for the adsorption of methanol and a catalyst for an equilibrium conversion of said lean gas stream to methanol, said catalyst and said adsorbent being uniformly distributed throughout said first fixed bed and withdrawing an effluent stream at about said reaction pressure comprising hydrogen, simultaneously depressurizing and purging said first fixed bed to a desorption pressure and recovering a crude methanol stream comprising methanol; and
  d) repeating steps (a) through (c) to provide a continuous process.

34. The process of claim 33 wherein said stoichiometric ratio of carbon to hydrogen ranges between about 2.2 and about 2.3.

35. The process of claim 33 wherein said oxygen containing stream comprises air and said effluent stream comprises nitrogen.

36. The process of claim 35 further comprising admixing said effluent stream with said lean synthesis gas stream prior to passing said lean gas stream to said compressor.

37. The process of claim 33 further comprising passing at least a portion of a second adsorber effluent from a second fixed bed at said reaction pressure to the first fixed bed to provide a third effluent comprising hydrogen prior to depressurizing the first fixed bed.

38. The process of claim 37 further comprising repressurizing said first fixed bed with at least a portion of said third effluent.

* * * * *